United States Patent [19]

Subramanian

[11] Patent Number: 5,549,882
[45] Date of Patent: Aug. 27, 1996

[54] IMAGING INFECTIOUS FOCI WITH HUMAN IGM 16.88

[75] Inventor: Ramaswamy Subramanian, Frederick, Md.

[73] Assignee: Akzo Nobel N.V., Arnhem, Netherlands

[21] Appl. No.: 346,988

[22] Filed: Nov. 30, 1994

Related U.S. Application Data

[63] Continuation of Ser. No. 899,661, Jun. 9, 1992, abandoned.
[51] Int. Cl.$^6$ .......................... A61K 49/00; A61K 51/00; G01N 33/569; C07K 16/00
[52] U.S. Cl. ........................ 424/1.11; 424/1.49; 435/7.1; 435/7.2; 435/7.32; 435/7.33; 435/7.34; 435/7.35; 435/7.36; 435/7.37; 530/391.3; 530/388.8; 530/389.7
[58] Field of Search ................................. 424/1.11, 1.49; 435/7.1, 7.2, 7.32, 7.33, 7.34, 7.35, 7.36, 7.37; 530/391.3, 388.8, 389.7

[56] References Cited

U.S. PATENT DOCUMENTS

| | | |
|---|---|---|
| 4,828,991 | 5/1989 | Hanna et al. . |
| 4,997,762 | 3/1991 | Hanna et al. . |
| 5,106,738 | 4/1992 | Hanna et al. . |

OTHER PUBLICATIONS

Steis et al. "Toxicity, Immunogenicity, and Tumor Radioimmunodetecting Ability of Two Human Monoclonal Antibodies in Patients with Metastatic Colorectal Carcinoma", J. Clin. Oncol., 8(3):476–490 (Mar. 1990).
Vallabhajosula et al, Journal of Nuclear Medicine, 33(5 supplement) Abstract No. 877, p. 1031 (May 1992).
Steis et al, Biological Abstracts, 89(11), Abstract No. 117429 (Jun. 1, 1990).
Ryan et al, Radiology, 167(1):71–75 (Apr. 1988).
Goldenberg et al, "In–vivo antibody imaging for detection of human tumors" in Cancer Imaging with Radiolabeled Antibodies, Goldenberg, Ed., pp. 273–292 (1990).
Subramanian et al., "Bioconjugate Chemistry," 3, 248–255 (1992).
Tzen et al., Journal of Nuclear Medicine, 21, 31–35 (1980).
Fischman et al., Journal of Nuclear Medicine, 31, 1199–1205 (1990).
Rubin et al., "The New England Journal of Medicine," 321, 14, 935–939 (1989).

*Primary Examiner*—Margaret Parr
*Assistant Examiner*—F. Christopher Eisenschenk
*Attorney, Agent, or Firm*—William M. Blackstone; Mary E. Gormley

[57] ABSTRACT

A method for imaging foci of infection by administering radiolabeled human IgM 16.88.

4 Claims, 2 Drawing Sheets

IMAGING INFECTIOUS FOCI WITH HUMAN IGM 16.88

This is a continuation of application Ser. No. 07/899,661 filed Jun. 9, 1992, now abandoned.

This invention relates to imaging sites of infections using human IgM 16.88, a human monoclonal antibody raised especially for targeting antigens associated with colorectal carcinoma tumors. Surprisingly, this monoclonal antibody also localizes to the sites of infection and can be used for imaging inflammation resulting from various conditions and diseases, including autoimmune diseases.

BACKGROUND OF THE INVENTION

Recently there has been an increase in the use of monoclonal antibodies for diagnostic and therapeutic applications in vivo. Successful attempts have been made to locate tumor lesions of size >5 mm using radiolabeled monoclonal antibodies and gamma camera imaging. It was hypothesized that in most of these cases specific antigen binding at the tumor site was responsible for the localization of radiolabeled antibody.

In 1988 Rubin et al. discovered the use of radiolabeled, non-specific polyclonal human immunoglobulin for the detection of focal inflammation by scintigraphy (Rubin, R. H., Fischman, A. J., Callahan, R. J. et al., "In(111) Labeled Nonspecific Immunoglobulin Scanning in the Detection of Focal Infection", N. Eng. J. Med., 1989, 30:385–389). It was shown that In(111)-IgG was superior to other radiopharmaceuticals such as Ga(67)-citrate and In-111 labeled white blood cells. Several other investigators have also found that radiolabeled polyclonal IgG localizes well in infectious foci.

The reason for localization of these radiopharmaceuticals in infection is not well understood. In the case of Ga(67)-citrate, the protein leakage of the radiometal may be responsible for the localization of Ga(67)-transferrin at the infectious sites (Tzen, K. Y., Oster, Z. H., Wagner, H. N., et al., "Role of Iron-Binding Proteins and Enhanced Vascular Permeability in the Accumulation of Gallium-67", Journal of Nuclear Medicine, 1980:21, 31–35.) Rubin et al. had considerable success using radiolabeled human polyclonal IgG antibodies in clinical trials. They further showed that Fab fragments of IgG did not localize to the infectious sites, whereas IgG and Fc fragments did. They also reported that the localization of In(111) labeled IgG substantially exceeded the localization of other compounds such as TC(99) labeled human serum albumin and Ga(67)-citrate (Fischman, A. L., Rubin, R. H., White, J. A., et al. "Localization of Fc and Fab Fragment of Nonspecific Polyclonal IgG at Focal Sites of Inflammation," J. Nucl. Med., 1990:31, 1199–1205). The blood clearance half-times ($t_{1/2}$) in hours were:

IgG—36.4

Fc—32.5

½Fc—22.3

Fab—12.8

Because of the fast clearance times one would expect ½Fc and/or Fab to be superior to IgG or Fc for imaging infections. However, animal experiments clearly showed that ½Fc and Fab fragments are relatively poor infection imaging agents.

SUMMARY OF THE INVENTION

This invention is a method for imaging foci of infection using radiolabeled human IgM 16.88.

BRIEF DESCRIPTION OF THE DRAWINGS

FIG. 1 illustrates imaging of inflammation in rabbits using In(111) labeled polyclonal IgG.

FIG. 2 illustrates imaging of inflammation in rabbits using In(111) labeled IgM 16.88.

DESCRIPTION OF PREFERRED EMBODIMENTS

Figure 1A:
FIGS. 1a and 1b are images at 4 hours.

The present invention demonstrates the use human monoclonal antibody 16.88 of isotype IgM in imaging of infectious foci. Furthermore, this invention shows that In(111) labeled 16.88 is superior to In(111) labeled human polyclonal IgG and In(111) labeled human monoclonal IgG for imaging of infectious sites. Human monoclonal antibody 16.88 is produced by the cell line LiCo 16.88, deposited with the American Type Culture Collection, Rockville, Md., U.S.A., Accession Number HB 8495, claimed in U.S. Pat. No. 4,997,762, which is included herein in its entirety by reference.

Often external imaging of lesions and infections depends on the target to non-target ratio of the radiopharmaceutical under investigation. In general, the larger the ratio the better the quality of the image. In imaging infectious foci this is of particular importance due to the non-specificity associated with the localization of immunoglobulins. The biological half life of IgM antibodies is 5 days, which is relatively short when compared with the half life of IgG antibodies (23 days) (Immunology Immunopathology and Immunity, Stewart Sell, 4th Edition, Elsevier, N.Y., 1987, pp. 87).

EXAMPLE I

Human monoclonal antibodies were produced by Epstein-Barr virus transformed human lymphoblastoid cell lines derived from peripheral blood lymphocytes of colon carcinoma patients immunized with autologous tumor vaccines by methods taught in U.S. Pat. Nos. 4,828,991 and 5,106,738, which are also included herein by reference.

Five different antibody preparations were analyzed with reference to their ability to localize in infectious foci. Note that LiLo refers to a novel bifunctional chelating agent suitable for attaching radiometals such In(111) to monoclonal antibodies (Subramanian, R., Colony, J., Shaban, S., Sidrak, H., Haspel, M. V., Pomato, N, Hanna, Jr., M. G. and McCabe, R. P., "New Chelating Agent for Attaching Indium-111 to Monoclonal Antibodies: In Vitro and In Vivo Evaluation", Bioconjugate Chemistry, 1992 3, 248–255 and application U.S. Ser. No. 07/773,753 by Subramanian et al., both of which are also included herein by reference. CO126CV154, CO126CV64 and CO126MV163 were obtained from Organon Teknika Corporation/Cappel, Westchester, Pa.

1. IgM—16.88-LiLo
2. IgG—CO126CV154-LiLo
3. IgG—CO126CV64-LiLo
4. IgG—CO126MV163-LiLo
5. IgG polyclonal-LiLo Preparation of In(111)-antibodies:

0.1 ml of antibody-LiLo complex (0.6–0.8 mg) was labeled with 0.4 mCi of In(111) using acetate and citrate buffers. A small amount of DTPA was added at the end of the reaction to scavenge unbound In(111), and the reaction mixture was purified by G50-70 gel filtration chromatography. The percentage of In(111) bound to the antibody was determined using ascending thin layer chromatography (solvent system: 50/50 mixture of methanol and 0.1M ammonium acetate buffer solution). For all preparations the labeling efficiency (LE) was >95% (Table 1).

Animal Model:

Male rats (100–120 g) were injected in the right thigh muscle with 0.1 ml of cell suspension containing 2×10E(6) E. coli per ml. The left leg served as a control. The rats developed severe infection within 24 hours as indicated by swelling of the right thigh and inability to use the leg.

Results:

All images were read qualitatively on a scale of +, 1+, 2+, 3+ based on the intensity of radioactivity at the site of infection. The results are shown in Table 2. Analysis of the image data revealed that all antibody preparations localized at the infectious site. However, greater than 70% of the images with IgM were graded at the highest level and showed less soft tissue uptake compared with IgG images. No differences were observed between monoclonal IgG and polyclonal IgG images.

Figure 1B:
Figure 1C:
FIGS. 1c and 1d are images at 24 hours.
Figure 1D:
Figure 2A:
FIGS. 2a and 2b are images at 4 hours.
Figure 2B:
Figure 2C:
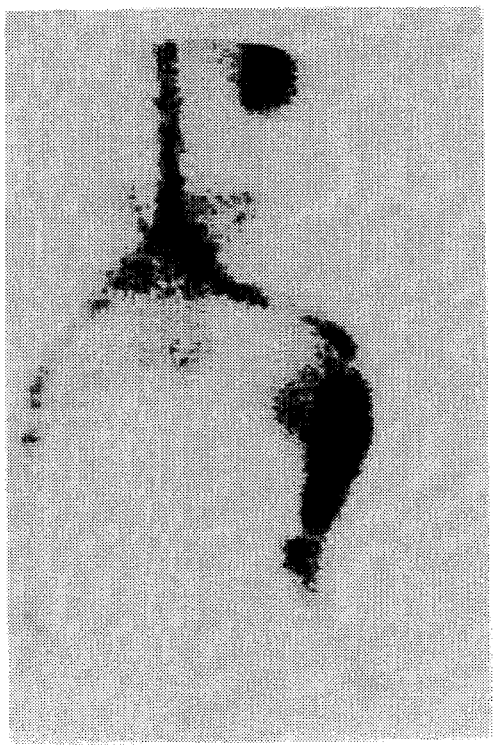
FIGS. 2c and 2d are images at 24 hours.
Figure 2D:
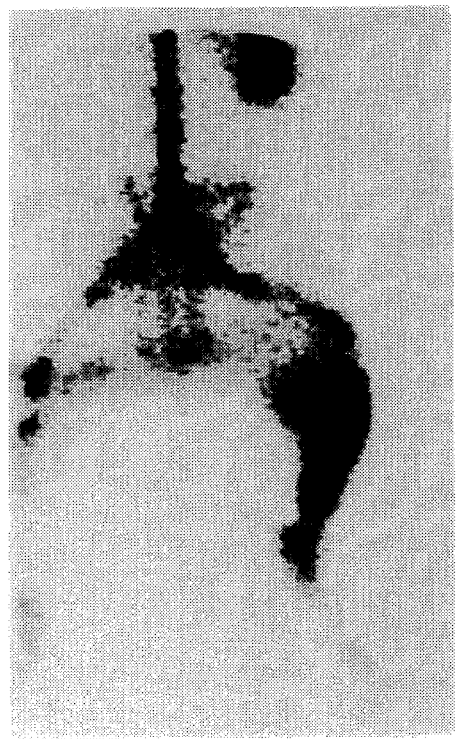

The above results were also confirmed using rabbit models. The images with In(111)-16.88 were the best at 4 hours with higher target/soft tissue ratios. The right leg in each rabbit can be seen to provide the denser image in the area inflammation compared with the left leg. The images of the polyclonal IgG in FIG. 1 and the monoclonal IgM in FIG. 2 demonstrated that the IgM provides significantly less nonspecific background binding at both the 4 hour and 24 hour images. Also, the comparative image density between the right leg with the infectious foci and the left leg, which was free of inflammation, provided significantly greater comparative image density using 16.88.

Any radioactive labels useful for imaging can be used for labeling human IgM 16.88. In the preferred embodiment, In(111) is the radioactive label. However, Tc(99), Cu(67), Ga(67), I(123) and I(131) may also be used for imaging infectious foci. Such use of these radioactive labels is taught in the prior art discussed above.

The labeled IgM 16.88 is administered by conventional means. Most normally intravenous administration is used, although intraperitoneal administration is preferred when the infection is exposed to the peritoneal cavity.

Conventional quantities of labeled IgM 16.88 are used for imaging. Preferably, approximately 5 mCi/70 Kg of body weight is administered. Overall, effective imaging should be obtainable through administering about 1 to 10 mCi/70 Kg. The preferred range is 2 to 5 mCi/70 Kg of body weight. Of course, as well known in the art, smaller overall quantities may be used when administering to known sites of infection. The labeled conjugates are prepared as described in Subramanian et al., Supra. Screening is conducted using a planar gamma scintillation camera. Methods for administration and scanning useful with the invention are the same as those taught by Steis, R. G. et al., "Toxicity, Immunogenicity, and Tumor Radioimmunodetecting Ability of Two Human Monoclonal Antibodies in Patients with Metastatic Colorectal Cancer," J. Clin. Oncol. 8(3), 476–490 (1990), for which purpose this article is to be included herein by reference.

The essence of this invention is the discovery of a human IgM antibody obtained from human B-cells taken from colorectal cancer patients immunized using autologous tumor vaccines, which is well known for its specificity to colorectal carcinoma associated antigens, being useful for imaging sites of infection. Accordingly, radioactive labels, chelators and methods of administration known in the art that are used to facilitate the imaging of infectious foci with human IgM 16.88 are believed to be well within the scope of the invention as set forth in the claims that follow.

TABLE 1

IMAGING STUDIES IN RATS WITH INFECTION

| Date | Tracer | L.E.* % | # Rats | Imaging studies performed at | | | | |
|---|---|---|---|---|---|---|---|---|
| | | | | 0.5 | 1 | 2 | 4 | 24 hrs. |
| 07/10/91 | IgM 16.88 | 97.9 | 5 | X | X | X | X | X |
| | IgG-CV154 | 98.4 | 5 | X | X | X | X | X |
| 07/11/91 | IgM 16.88 | 96.4 | 8 | | | | X | X |
| | IgG-CV154 | 96.8 | 7 | | | | X | X |
| 07/12/91 | IgG-MV163 | 95.5 | 7 | | | | X | X |
| | IgG-CV64 | 51.3 | not studied in animals | | | | | |
| 08/14/91 | IgG-CV64 | 97.2 | 6 | | | | X | X |
| | IgG-poly | 98.1 | 7 | | | | X | X |

*labeling efficiency

TABLE 2

Results of In-Antibody Imaging Data

| Date of Test | Tracer | # Rats | Time of Imaging Study (hr) | Uptake** | | | | Fraction Positive (2+ or greater) |
|---|---|---|---|---|---|---|---|---|
| | | | | + | 1+ | 2+ | 3+ | |
| 06/27/91 | In-LiLo | 3 | 0.25 | | | | | 0/3 |
| | | | 0.5 | | | | | 0/3 |
| | | | 1 | | | | | 0/3 |
| | | | 2 | | | | | 0/3 |
| | | | 4 | | | | | 0/3 |
| 06/27/91 | In-TF* | 4 | 2 | 1 | 1 | 2 | | 2/4 |
| | | | 4 | | 1 | 2 | 1 | 3/4 |
| | | | 24 | 1 | 1 | 1 | 1 | 2/4 |
| 07/12/91 | ⁶⁷Ga-Citrate | 6 | 4 | | | 2 | 4 | 4/6 |
| 07/10/91 | In-IgM 16.88 | 5 | 4 & 24 | | | 3 | 1 | 4/5 |

TABLE 2-continued

Results of In-Antibody Imaging Data

| Date of Test | Tracer | # Rats | Time of Imaging Study (hr) | Uptake** + | 1+ | 2+ | 3+ | Fraction Positive (2+ or greater) |
|---|---|---|---|---|---|---|---|---|
| 07/11/91 | In-IgG | 5 | 4 & 24 | | | 3 | | 3/5 |
| | In-IgM 16.88 | 7 | 4 | | 2 | 5 | | 5/7 |
| | | | 24 | | 1 | 2 | 4 | 6/7 |
| | In-IgG CV154 | 6 | 4 | | 2 | 4 | | 4/6 |
| | | | 24 | | 1 | 3 | 2 | 5/6 |
| 07/12/91 | In-IgG MV163 | 7 | 4 | | 4 | 2 | | 2/7 |
| | | | 24 | | 1 | 3 | 1 | 4/7 |
| 8/14/91 | In-IgG CV64 | 6 | 4 | | 1 | 3 | 2 | 5/6 |
| | | | 24 | | 1 | 4 | 1 | 5/6 |
| | In-IgG-poly | 7 | 4 | | 2 | 4 | 1 | 5/7 |
| | | | 24 | | 2 | 5 | | 5/7 |

*Transferin
**2+ Uptake Cutoff for Positive Image

TABLE 3

IMAGING STUDIES IN RABBITS WITH INFECTION: COMPARISON OF 3 In(111) LABELED ANTIBODIES WITH In(111) TRANSFERRIN

| Date | Tracer | L.E. (%) | # Rabbits | Imaging studies performed at 4 hrs. | 24 hrs. |
|---|---|---|---|---|---|
| 11-20-91 | IgM-16.88 | 97.5 | 2 | X | X |
| | IgG-CV64 | 98.0 | 2 | X | X |
| | IgG-poly | 97.5 | 2 | X | X |
| | In-TF (plasma) | | 2 | X | X |

We claim:

1. A method for locating bacterial infectious loci in an animal comprising the administration of radiolabelled human IgM monoclonal antibody 16.88, having ATCC accession number 8495, to the animal in an amount effective for detection and identification of said infectious foci and detecting the radiolabelled antibody thereby locating said infectious foci.

2. The method of claim 1, wherein the human IgM 16.88 is radiolabeled with a radionuclide selected from the group consisting of Tc(99), Cu(67), Ga(67), I(123), I(131) and In(111).

3. The method of claim 2, wherein the radionuclide is In(111).

4. The method of claim 1, wherein the animal is a man.

* * * * *

UNITED STATES PATENT AND TRADEMARK OFFICE
CERTIFICATE OF CORRECTION

PATENT NO. : 5,549,882
DATED      : August 27, 1996
INVENTOR(S) : Ramaswamy Subramanian It is certified that error appears in the above-indentified patent and that said Letters Patent is hereby corrected as shown below:

Column 6:

In claim 1, line 1, delete "loci" and replace with -- foci --;

and line 4, after "8495", delete "." and replace with -- , --.

Signed and Sealed this

Fifth Day of November, 1996

*Attest:*

BRUCE LEHMAN

*Attesting Officer*  *Commissioner of Patents and Trademarks*